United States Patent
Lev et al.

(10) Patent No.: US 12,343,238 B2
(45) Date of Patent: Jul. 1, 2025

(54) WOUND DRESSING COMPRISING A COMBINATION OF HYDROGEL AND HONEY, METHOD OF PREPARATION AND USES THEREOF

(71) Applicant: Sion Biotext Medical Ltd., Sderot (IL)

(72) Inventors: Daniel Lev, Western Galilee (IL); Yulia Holenberg, Ramat Hagolan (IL)

(73) Assignee: Sion Biotext Medical Ltd., Sderot (IL)

( * ) Notice: Subject to any disclaimer, the term of this patent is extended or adjusted under 35 U.S.C. 154(b) by 493 days.

(21) Appl. No.: 17/777,955

(22) PCT Filed: Nov. 19, 2020

(86) PCT No.: PCT/IL2020/051200
§ 371 (c)(1),
(2) Date: May 18, 2022

(87) PCT Pub. No.: WO2021/100045
PCT Pub. Date: May 27, 2021

(65) Prior Publication Data
US 2023/0032299 A1 Feb. 2, 2023

(30) Foreign Application Priority Data
Nov. 19, 2019 (IL) .......................................... 270762

(51) Int. Cl.
*A61F 13/00* (2024.01)
*A61F 13/01* (2024.01)
(Continued)

(52) U.S. Cl.
CPC .. *A61F 13/00063* (2013.01); *A61F 13/01008* (2024.01); *A61K 35/644* (2013.01);
(Continued)

(58) Field of Classification Search
None
See application file for complete search history.

(56) References Cited

U.S. PATENT DOCUMENTS

| 5,065,752 A | 11/1991 | Sessions et al. |
| 6,162,864 A | 12/2000 | Tanihara et al. |
| (Continued) | | |

FOREIGN PATENT DOCUMENTS

| CN | 203577000 U | 5/2014 |
| CN | 108144109 A | 6/2018 |
| (Continued) | | |

OTHER PUBLICATIONS

Translation of CN 108404202 A (Year: 2018).*
(Continued)

*Primary Examiner* — Kim M Lewis
(74) *Attorney, Agent, or Firm* — GREENBERG TRAURIG, LLP

(57) ABSTRACT

The present disclosure provides a wound dressing composition comprising cross-linked hydrogel scaffold and embedded therein anti-bacterially active honey, said activity being determined by the detection of hydrogen peroxide production rate by said wound dressing; said wound dressing further comprising at least one of a photo-initiator and/or at least one UV cross linker, the total amount of said photo-initiator and/or UV cross linker is equal or less than 0.2% w/w out of the total weight of the wound dressing. Also disclosed herein is a method of preparing the wound dressing and methods of using the same with respect to wounds, the method of preparation comprises mixing a hydrogel forming mixture comprising hydrogel forming monomer or monomers, honey and at least one photo-initiator and/or at least one UV cross-liker to form a homogenous mixture; and
(Continued)

subjecting the homogenous mixture to UV irradiation until said homogenous mixture solidifies.

16 Claims, 8 Drawing Sheets

(51) Int. Cl.
  *A61K 35/644* (2015.01)
  *A61L 15/40* (2006.01)
  *A61L 15/44* (2006.01)
  *A61L 26/00* (2006.01)

(52) U.S. Cl.
  CPC .............. *A61L 15/40* (2013.01); *A61L 15/44* (2013.01); *A61L 26/0009* (2013.01); *A61L 26/008* (2013.01); *A61F 2013/00161* (2013.01); *A61L 2300/404* (2013.01)

(56) References Cited

U.S. PATENT DOCUMENTS

| | | | |
|---|---|---|---|
| 6,881,789 | B2 | 4/2005 | Bosse |
| 6,956,144 | B2 | 10/2005 | Molan |
| 7,511,083 | B2 | 3/2009 | Madsen et al. |
| 7,714,183 | B2 | 5/2010 | Caskey |
| 8,632,810 | B2 | 1/2014 | Moloney |
| 9,107,974 | B2 | 8/2015 | Payne et al. |
| 9,211,358 | B2 | 12/2015 | Sinko et al. |
| 11,213,569 | B2 * | 1/2022 | Hamed ................. A61K 8/042 |
| 2003/0143274 | A1 | 7/2003 | Viegas et al. |
| 2004/0153040 | A1 | 8/2004 | Martineau et al. |
| 2011/0135726 | A1 | 6/2011 | Munro et al. |
| 2014/0039423 | A1 | 2/2014 | Riesinger et al. |
| 2014/0336557 | A1 | 11/2014 | Durdag et al. |
| 2016/0339141 | A1 | 11/2016 | Gann |
| 2017/0209500 | A1 | 7/2017 | Moloney et al. |
| 2018/0110900 | A1 | 4/2018 | Korenfeld |
| 2018/0161476 | A1 | 6/2018 | MacDonald et al. |
| 2021/0069377 | A1 * | 3/2021 | Kershaw ................. A61L 27/54 |
| 2021/0361492 | A1 * | 11/2021 | Wibaux ............. A61F 13/0203 |

FOREIGN PATENT DOCUMENTS

| | | | |
|---|---|---|---|
| CN | 108404202 A * | 8/2018 | |
| EP | 1237561 B1 | 3/2004 | |
| EP | 3351665 A1 | 7/2018 | |
| EP | 3253424 B1 | 12/2020 | |
| GB | 2322078 A | 8/1998 | |
| GB | 2 527 617 A | 12/2015 | |
| KR | 20190079073 A * | 7/2019 | |
| RU | 20140200 A1 * | 10/2015 | |
| WO | 2001015750 A1 | 3/2001 | |
| WO | 2004089431 A2 | 10/2004 | |
| WO | 2006037606 A2 | 4/2006 | |
| WO | 2014074503 A1 | 5/2014 | |
| WO | 2015059501 A1 | 4/2015 | |
| WO | 2017147067 A1 | 8/2017 | |
| WO | 2018050764 A1 | 3/2018 | |
| WO | 2018091890 A1 | 5/2018 | |

OTHER PUBLICATIONS

Translation of RS 20140200 A1 (Year: 2015).*
Translation of KR 20190079073 A (Year: 2019).*
Mandal et al., Honey: its medicinal property and antibacterial activity, Apr. 2011, Asian Pacific Journal of Tropical Biomedicine, 1(2) :154-160, Abstract. (Year: 2011).*
International Search Report and Written Opinion from International Application No. PCT/IL2020/051200 dated Feb. 22, 2021.
Oryan et al., "Biological properties and therapeutic activities of honey in wound healing: A narrative review and meta-analysis" Journal of Tissue Viability (2016) 25(2), 98-118.
Abu-Jdayil et al., "Heat effect on rheology of light- and dark-colored honey" Journal of Food Engineering 51(1), 33-38.
Biluca et al., "5-HMF and carbohydrates content in stingless bee honey by CE before and after thermal treatment" Food Chemistry (2014) 159, 244-249.
Dag et al., "Physical, chemical and palynological characterization of avocado (*Persea americana* Mill.) honey in Israel" International Journal of Food Science and Technology (2005) 40, 1-8.
Petrov, V. "Mineral constituents of some Australian honeys as determined by atomic absorption spectrophotometry". Journal of Apicultural Research (1970) 9, 95-101.
Da Silva et al. "Honey: Chemical composition, stability and authenticity" Food Chemistry (2016) 196, 309-323.
Henriques et al. "Free radical production and quenching in honeys with wound healing potential" Journal of Antimicrobial Chemotherapy (2006) 58, 773-777.
Nalampang et al "Design and Preparation of AMPS-Based Hydrogels for Biomedical Use as Wound Dressings" Chiang Mai J. Sci. (2007) 34(2), 183-189.
Golon et al., "Characterization of "caramel-type" thermal decomposition products of selected monosaccharides including fructose, mannose, galactose, arabinose and ribose by advanced electrospray ionization mass spectrometry methods". Food Funct. (2013) 4(7), 1040-50.
Simkovic et al., "Primary reactions of sucrose thermal degradation" J. Anal. Appl. Pyrolysis (2003) 70, 493-504.
Sohaimy et al., "Physicochemical characteristics of honey from different origins" Annals of Agricultural Sciences (2015) 60 (2), 279-287.
Durmaza et al., "Acrylamide/2-acrylamido-2-methylpropane sulfonic acid sodium salt-based hydrogels: synthesis and characterization" Polymer (2000) 41, 3693-3704.
Oroian et al., "Multi-Element Composition of Honey as a Suitable Tool for Its Authenticity Analysis" Pol. J. Food Nutr. Sci., (2015) 65(2), 93-100.
White Jr. JW "Honey" Advances in Food Research (1978) 24, 287-374.
Al-Waili et al., "Honey for wound healing, ulcers, and burns; Data Supporting Its Use in Clinical Practice", The Scientific World Journal (2011) 11, 766-787.
El-Kased et al. "Honey-based hydrogel: In vitro and comparative In vivo evaluation for burn wound healing", Scientific Reports, 7-9692, pp. 1-11.

* cited by examiner

WOUND DRESSING COMPRISING A COMBINATION OF HYDROGEL AND HONEY, METHOD OF PREPARATION AND USES THEREOF

RELATED APPLICATIONS

The present application is a national phase filing under 35 USC 371 of International Application No. PCT/IL2020/051200, filed on Nov. 19, 2020, which claims priority of Israeli Patent Application No. 270762, filed on Nov. 19, 2019, the contents of which are incorporated herein in their entirety for all purposes.

TECHNOLOGICAL FIELD

The present disclosure relates to wound dressings.

BACKGROUND ART

References considered to be relevant as background to the presently disclosed subject matter are listed below:

Ahmad Oryan et al "*Biological properties and therapeutic activities of honey in wound healing: A narrative review and meta-analysis*" Journal of Tissue Viability (2016) 25 (2), 98-118

Abu-Jdayil A, Al-Majeed Ghzawi A, Al-Malah K I M, Zaitoun S "*Heat effect on rheology of light-and dark-colored honey*" Journal of Food Engineering (2000) 51 (1), 33-38

F C Biluca, F D Betta, G Pirassol de Oliveira, L M Pereira, L Valdemiro Gonzaga, A C Oliveira Costa, F Fett "*5-HMF and carbohydrates content in stingless bee honey by CE before and after thermal treatment*" Food Chemistry (2014) 159, 244-249

Dag A, Afik O Yeselson Y, Schaffer A, Shafir S "*Physical, chemical and palynological characterization of avocado (Persea americana Mill.) honey in Israel*" International Journal of Food Science and Technology (2005) 40, 1-8

Petrov, V. "*Mineral constituents of some Australian honeys as determined by atomic absorption spectrophotometry*". Journal of Apicultural Research (1970) 9, 95-101.

Priscila Missio da Silva et al. "*Honey: Chemical composition, stability and authenticity*" Food Chemistry (2016) 196, 309-323

Neil Burton et al. "*Free radical production and quenching in honeys with wound healing potential*" Journal of Antimicrobial Chemotherapy (2006) 58, 773-777

Chinese patent application publication No. 108144109

Kanarat Nalampang et al "*Design and Preparation of AMPS-Based Hydrogels for Biomedical Use as Wound Dressings*" Chiang Mai J. Sci. (2007) 34 (2), 183-189

A Golon, N Kuhnert "*Characterization of "caramel-type" thermal decomposition products of selected monosaccharides including fructose, mannose, galactose, arabinose and ribose by advanced electrospray ionization mass spectrometry methods*". Food Funct. (2013) 4 (7), 1040-50.

I Simkovic, I Surina, M Vrican "*Primary reactions of sucrose thermal degradation*" J. Anal. Appl. Pyrolysis (2003) 70, 493-504

El Sohaimy S A, Masry S H D, Shehataa M G "*Physicochemical characteristics of honey from different origins*" Annals of Agricultural Sciences (2015) 60 (2), 279-287

S. Durmaza and O. Okay "*Acrylamide/2-acrylamido-2-methylpropane sulfonic acid sodium salt-based hydrogels: synthesis and characterization*" Polymer (2000) 41, 3693-3704

Oroian M, Amariei S, Leahu A, Gutt G "*Multi-Element Composition of Honey as a Suitable Tool for Its Authenticity Analysis*" Pol. J. Food Nutr. Sci., (2015) 65 (2), 93-100

White Jr. J W "*Honey*" Advances in Food Research (1978) 24, 287-374

International Patent Application Publication No. WO2015/059501

Al Waili N S et al. "Honey for Wound Healing, Ulcers, and Burns; Data Supporting Its Use in Clinical Practice" The Scientific World JOURNAL (2011) 11, 766-787

Acknowledgement of the above references herein is not to be inferred as meaning that these are in any way relevant to the patentability of the presently disclosed subject matter.

BACKGROUND

Honey has been described as having antimicrobial, anti-inflammatory and antioxidant activities, contributing to debridement action, stimulating wound regeneration and accelerating wound healing processes. This activity can be explained by slow release of hydrogen peroxide due to interaction of wound exudates with the honey's inherent glucose oxidase, high osmolality, acidity, high content of phenols, lymphocyte and antibody production and others [Oryan et al. 2016].

In order to preserve biological activity of honey, it should be stored, processed and handled at as low temperature as possible. As a function of honey type and origin, temperature stability of honey can vary. At temperatures, which are higher than 40° C., biological activity of the most types of honey is affected. At these temperatures, the formation of undesirable products, such as toxic 5-hydroxymethylfurfural (HMF) [e.g. Biluca et al, 2014] occurs. The elements occur due to the reaction of the carboxylic group on the reducing end of sugars and the free amino groups of amino acids and proteins, which are present in honey (Maillard reaction). [da Silva et al., 2016].

Data supporting its use in clinical practice, such as in treatment of wounds, ulcers and burns, is also available [Al Waili et al. 2011]

Glucose oxidase, which produces hydrogen peroxide, remains stable at a temperature of up to 55° C., while at 55-70° C. it decomposes. Other active properties can be affected already at 37° C. [Oryan et al., 2016].

Honey-impregnated wound dressings was described with emphasis on free radical production of some honey [Burton et al., 2006].

CN 108144109 describes a honey-containing hydrogel dressing with an interpenetrating network cross-linked structure. The hydrogel dressing with the interpenetrating network cross-linked structure is described to be high in strength and not easily disintegrated after absorbing water. The hydrogel is further described as having efficient instantaneous absorption speed and sustainable absorption capacity and can be used for wound with more seepage. According to this publication, metal ions inside honey participate in cross-linking of hydrogel, and honey is difficult to dilute and separate out. Cross-linking reaction occurs at high temperatures of 40° C.-60° C. (temperatures at which the enzymes within the honey are destroyed). It is described that the honey-containing hydrogel dressing display oxidation resistance (this being due to the high temperature treatment of the honey) and bacteriostatic activity and provides moist healing environments for the wound, and the hydrogel dressing can be used for preparing medical supplies and has a good market prospect.

Sheet-hydrogel technology lets develop and manufacture products for advanced wound care with fluid absorption, moist healing environment maintenance and other properties under full control of the process [Nalampang., et al. 2007]. Cross-linking under UV (free radical polymerization) provides cold-processing manufacturing of hydrogels, which let introduce honey to the hydrogels. However, this process requires use of chemical photo-initiators and cross-linker, which can worsen hydrogel biocompatibility.

Wound dressings comprising a backing layer having disposed thereon a discontinuous layer of hydrogel are described in WO2015/059501, wherein the discontinuous layer of hydrogel is in the form of discrete islands of hydrogel.

GENERAL DESCRIPTION

The present disclosure is based on the finding that the incorporation of honey in cold processes of manufacturing of hydrogels allows for the significant reduction of the amount of or need for chemical photo-initiators and cross linkers, while preserving the enzymatic activity of the honey within the hydrogel, thereby providing a wound dressing with improved biocompatibility. In fact, the presence of honey prior to cross-linking allowed to overcome the need to use high amounts of cross-linkers and polymerization initiators (e.g. UV photo-initiators) and thereby provide a safer wound dressing.

Thus, the present disclosure aims at providing a wound dressing composition containing biologically active honey (e.g. a honey that is recognized as having wound healing properties) and having improved biocompatibility and improved primary wound care, as further described below.

Specifically, there is disclosed herein a wound dressing composition comprising cross-linked hydrogel scaffold and embedded therein anti-bacterially active honey, said activity being determined by the detection of hydrogen peroxide production rate by said wound dressing, the wound dressing composition comprising least one of a photo-initiator and/or at least one UV cross linker, with a total amount of said photo-initiator and/or UV cross linker being equal or less than 0.2% w/w out of the total weight of the wound dressing.

Also disclosed herein is a method of producing a wound dressing composition comprising cross-linked hydrogel scaffold and embedded therein anti-bacterially active honey, the method comprising mixing a mixture comprising hydrogel forming monomer or monomers, honey and at least one photo-initiator and/or at least one UV cross-liker to form a homogenous mixture; and subjecting the homogenous mixture to UV irradiation until said homogenous mixture solidifies. In one preferred case, the mixture comprises an amount of said photo-initiator and/or UV cross linker that is equal or less than 0.2% w/w out of the total weight of the wound dressing composition.

In addition, disclosed herein is a method of treating a wound, e.g. an infected wound, the method comprises placing a wound dressing composition disclosed herein onto the wound.

A further method disclosed herein concerns the prevention of wound infection, the method comprising placing the wound dressing composition disclosed herein onto a wound in predisposition of developing infection, e.g. post surgery.

The present disclosure also provides a kit comprising the wound dressing composition disclosed herein and instructions for use thereof in wound dressing.

Finally, disclosed herein is a method of providing an anti-microbial cross-linked hydrogel that can be used as the wound dressing disclosed herein, the method comprises mixing a mixture comprising cross-linkable hydrogel forming monomer and honey and exposing the mixture to UV radiation until the mixture solidifies.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
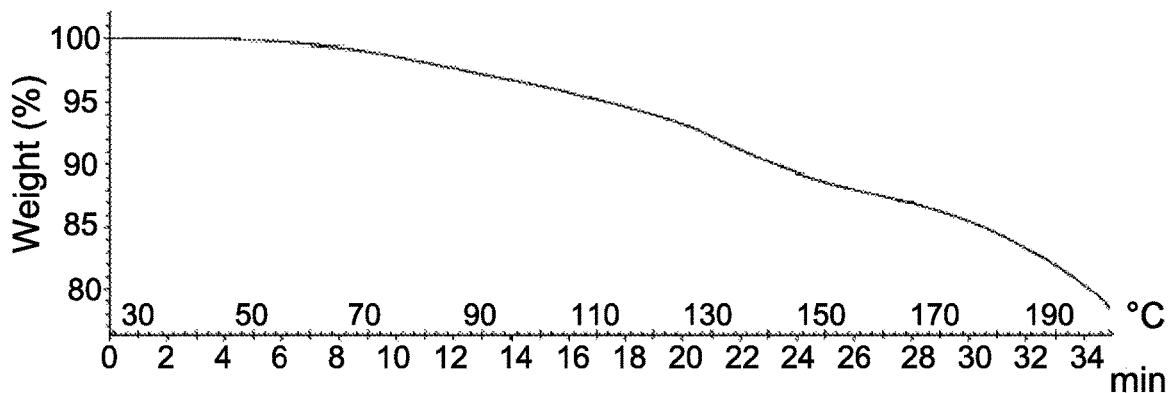
FIGS. 1A-1B provide TGA results of LMesitran Medicinal Honey defining monomer content, where FIG. 1A provides TG, i.e. the % weight (weight %) of the LMesitran Medicinal Honey versus temperature (° C.) and FIG. 1B provides DTG, i.e. % weight change in time (%/min) of the LMesitran Medicinal Honey versus temperature, both Figures being at a heating rate of 5° C./min.

The present disclosure provides compositions which can be used as wound dressings that comprise a cross-linked hydrogel scaffold and honey that is embedded within the scaffold, the wound dressing composition exhibited anti-bacterial activity that is considered to be ascribed to the activity of enzymes from the honey. Further, the anti-bacterial activity can be assayed or confirmed by the detection of hydrogen peroxide production rate by the wound dressing, as further discussed hereinbelow.

Surprisingly, in the presence of the honey, the wound dressing composition is formed in the presence of a UV photo-initiator in an amount that is significantly lower than the amount thereof required in the absence of honey (see data from Table 1C, for example).

Also disclosed herein is a method of producing the wound dressing composition, the method comprises mixing a mixture comprising a hydrogel forming monomer or monomers, honey and at least one photo-initiator and/or at least one UV cross-liker to form a homogenous mixture; and subjecting the homogenous mixture to UV irradiation until the homogenous mixture solidifies. The amount of the at least one photo-initiator and/or at least one UV cross-liker is preferably equal or less than 0.2% w/w out of the total weight of the mixture (and of the eventual composition).

It has been envisaged that the exposure of the monomers to UV, in the presence of some amount (and relatively low amount) of a phono initiator and/or a cross linker, causes cross linking of the monomers, without damaging the biological functionality of the honey and specifically, its healing properties. In this connection, it is noted that it has been found that including honey allows to significantly reduce the amount of initiators and/or cross linkers used in order to cause cross-linking into a solid wound dressing, as compared to the amount thereof required in the absence of the honey. This is also emphasized in Table 1C below showing that in the absence of honey, the amount of either or both the initiator and cross linker are higher. In other words, in order to sufficiently solidify in the absence of honey, a higher amount of each or both are needed. For example, in the absence of honey, to reach an infinite viscosity (i.e. to sufficiently solidify) the total amount of the initiator and cross linker was 0.9% w/w. The same viscosity was achieved in the presence of between about 10% w/w to about 20% w/w honey and a total amount of the initiator and cross linker of about 0.2% w/w.

The finding disclosed herein was unexpected and provides a beneficial product as there is a desire to minimize the amount of initiators and/or cross-linkers remaining in the wound dressing and the inclusion of honey allowed for a significant reduction in the amount of same.

In addition, it was found that in the presence of the honey and even at these low amounts of initiator and/or cross linkers, all the monomers are cross-linked. This is considered one important feature of the wound dressing as there is a disadvantage in having a significant amount of free monomers in the composition, once applied onto the skin. In other words, the wound dressing preferably contains no detectable amounts of non-cross-linked monomer units of said the cross-linked hydrogel scaffold.

The presence of the honey together with the trace amounts of the at least one photo-initiator and/or cross linker allows to reach a desirable viscosity, notwithstanding the low amounts of the initiator and/or cross-linkers.

The viscosity of the wound dressing composition can be determined by conventional means, including commonly available viscometers.

In some examples, the viscosity is determined using a T-BAR T-F HBDV-E (or one such as Spindle R7 defined herein) with a rotating speed of about 12 rpm.

In some cases, the viscosity of the wound dressing composition disclosed herein is at least 15,000 cPs, at times, at least 30,000 cPs, at times, at least 50,000 cPs; at times, at least 100,000 cPs, at times, at least 200,000 cPs, at times, at least 300,000 cPs, at times, above 333,000 cPs.

The viscosity of the wound dressing composition can be determined, for example, using The healing property of honey is due to the fact that it offers antibacterial activity, maintains a moist wound condition, all together helping to provide a protective barrier to prevent infection of the wound. The antimicrobial activity is due to the enzymatic production of hydrogen peroxide. Some also report that anti-microbial activity of honey can be related to the low pH levels of honey and high sugar content (high osmolarity) that is enough to hinder the growth of microbes. This is seen, for example, in non-peroxide honey, such as Manuka honey. In addition, anti-microbial activity can be due to the presence of phytochemical components like methylglyoxal (MGO).

The antimicrobial agent (factor) in honey is predominantly the hydrogen peroxide entities, of which the concentration is determined by relative levels of glucose oxidase, synthesized by the bee and catalase originating from flower pollen.

Most types of honey generate $H_2O_2$ when diluted, because of the activation of the enzyme glucose oxidase that oxidizes glucose to gluconic acid and $H_2O_2$, which thus attributes the antimicrobial activity. But, in some cases and as also evident by the non-limiting examples provided herein, the peroxide activity in honey can be destroyed easily by heat or the presence of catalase.

Honey may retain its antimicrobial activity even in the presence of catalase (absence of glucose oxidase), and thus this type of honey is regarded as "non-peroxide honey". Several components are known to contribute the non-peroxide activity, such as the presence of methyl syringate and methylglyoxal (e.g. in manuka honey).

The correlation between color and anti-microbial potency of honey was discussed [Albaridi N A. Antibacterial Potency of Honey. Int J Microbiol. 2019; 2019:2464507. Published 2019 Jun. 2. doi: 10.1155/2019/2464507]. The color of honey ranges from light yellow, through to amber and dark reddish amber to a nearly black color. The color of honey may reflect various components present such as polyphenols, minerals, and pollen, with dark honey having a higher amount of pigments such as flavonoids Dark honey has a high level of phenolic compounds and this has been shown to have a good correlation with its higher antibacterial activity.

There are various ways to determine the antibacterial activity of honey, and most concentrate on the level or rate of production of hydrogen peroxide. For example, the hydrogen peroxide production rate can be determined by the use of a hydrogen peroxide test strips, used according to manufacturer's instruction. For example, the test strip can be dipped into the solution to be tested and after the prescribed time (typically seconds), identify the color of the strip vis-à-vis the predefined color scale.

The color of the honey also correlates with the honey mineral content. Light-colored honeys usually contain up to 0.2% metal ions and other colloidal matters, while dark-colored honeys can include 1% of metal ions or higher. In the current research monofloral Avocado honey have been used as a model for dark honey, while Acacia honey as a light honey. Potassium content, which is main mineral presented in honey, correlates with honey pigmentation, and reaches a mean level of 441 ppm for light honeys and 1676 ppm for dark honeys. Monofloral avocado honey may contain 3800 ppm of potassium in average, while acacia honey contains circa 550 ppm of potassium.

In some examples, the honey is a light honey. Without being bound thereto, light honey has lower bioburden and therefore, for sterilization validation and other requirements may be more feasible than dark honey.

In some examples, the honey is one having metal ion content of up to 0.2%.

Irrespective of the color of the honey, there are various types of honey that can be used for wound healing and thus within the wound dressing disclosed herein. These include, without being limited thereto, *Leptospermum scoparium* honey (e.g. Manuka, Medihoney—dark); Buckwheat honey (e.g. Principelle—dark), Acacia honey (light), Stingless bee honey (light), Chestnut honey (light amber), *Rhododendron* honey (light), *Eucalyptus* honey (light amber), Polyfloral honeys (various), medical grade honey (e.g. Revamil®, Vetramil®, L-Mesitran®, the latter comprising 40% medical grade honey, lanolin, propylene glycol, PEG 4000, vitamin C, vitamin E).

In the context of the present disclosure, a medical grade honey, or medicinal honey, is to be understood as encompassing any honey that is suitable or known to be suitable for application onto a wound. Such honey is typically recognized as one having a wound healing effect.

In some cases, the honey is one that is recognized has having anti-bacterial activity due to oxygen peroxide production or presence of glucose oxidate.

In some cases, the honey is mixed with a carrier, such as a medically or pharmaceutically acceptable lipophilic substance, e.g. oil, wax, etc.

In some cases, the medical grade (medicinal) honey is multi-floral honey without traces of known pesticides or insecticides and controlled microbiological content.

The amount of honey can vary, depending on the amount of initiators and/or cross linker used and the desired level of viscosity.

In some examples, the wound dressing composition comprises in the composition, at least 1% w/w honey, at times, at least 5% w/w honey, at times at least 8% w/w, at times, at least 10% w/w honey, at times, at least 12% w/w honey, at times at least 14% w/w honey, at times, at least 15% w/w honey, a times at least 18% w/w honey, at times, at least 20% w/w honey, at times at least 22% w/w, at times, at least 24% w/w honey, at times, at least 26% w/w honey, at times at least 28% w/w honey, at times, at least 30% w/w honey, a times at least 32% w/w honey; at times, at least 34% w/w honey, at times at least 36% w/w honey, at times, at least 38% w/w honey, at times, at least 40% w/w honey, at times at least 42% w/w honey, at times, at least 44% w/w honey, a times at least 46% w/w honey or even up to 50% w/w honey.

In some cases, the amount of honey is any amount within the range of 5% w/w and 50% w/w; at times, any amount between 5% w/w and 40% w/w; at times, any amount between 10% w/w and 40% w/w; at times, an amount of 20%±15% w/w.

The wound dressings (the composition per se as well as the composition on a support matrix) disclosed herein comprises a cross-linked hydrogel scaffold and embedded within the scaffold is the active honey. The cross-linking of the hydrogel is the result of UV irradiation in the presence of the honey and the initiator and/or cross linker, as opposed to heat induced cross-linking where heat is the driving force of the cross linking.

The manner (type) of cross linking can be evident in the final product, namely, the wound dressing composition, from the presence or absence of antibacterial activity (that would have been reduced or eliminated by thermal cross-linking) but also, optionally, by the presence of at least a trace amount (i.e. below 0.2% w/w) of a photo-initiator and/or UV-cross linker. The trace amount of either or both photo-initiator and UV-cross linker can be in the range of picomoles and may be regarded as one form of a fingerprint for distinguishing between hydrogels that are produced in accordance with the present disclosure and those produced by thermal polymerization (where there is no need for such agents).

A further fingerprint is provided by the antibacterial activity of the wound dressing due to the functionally/biologically active honey, as discussed herein.

Photo-initiators which can be used in the formation of the wound dressing and thus be present in the wound dressing of the present disclosure are well known in the art. Yet, without being bound thereto, the photo-initiator can be one or combination of 2-Hydroxy-2-methylpropiophenone, Ethyl (2,4,6-trimethylbenzoyl) phenyl phosphinate, Diphenyl(2,4,6-trimethylbenzoyl) phosphine oxide 10%-25%; 2-hydroxy-1-[4-(hydroxyethoxy)phenyl]-2-methyl-1-propanone, 1-hydroxycyclohexyl phenyl ketone, 2,2-dimethoxy-2-phenylacetophenone and others.

UV cross-linkers which can be used in the formation of the wound dressing and thus be present in the wound dressing of the present disclosure are also well known in the art. Yet, without being bound thereto, the UV cross-linker can be one or combination of methacryloxyethyl vinyl carbonate, NVP-AAM077 Tetrasodium Hydrate, N,N-methylenebisacrylamide, tetraethylene glycol Poly(ethylene glycol) methyl ether monomethacrylate, Tetra(ethylene glycol) dimethacrylate; ethylene glycol dimethacrylate, polyethylene glycol (400) diacrylate (Miramer M280), 4-(1-oxo-2-propenyl)-morpholin (Genocure ACMO).

In some cases, the wound dressing disclosed herein contains at least trace amounts of a photo initiator or of a UV cross-linker.

In the context of the present disclosure, when referring to at least trace amounts it is to be understood as a detectable amount and yet an amount that does not exceed 0.2% w/w out of the total weight of the material forming the composition (excluding any supporting matrix).

In some cases, the trace amount is an amount that does not exceed 0.19% w/w, at times, an amount that does not exceed 0.18% w/w, at times, an amount that does not exceed 0.17% w/w at times, an amount that does not exceed 0.16% w/w at times, an amount that does not exceed 0.15% w/w; at times, an amount that does not exceed 0.1%; at times, an amount that does not exceed 0.09%; at times, an amount that does not exceed 0.08%; at times, an amount that does not exceed 0.07%; at times, an amount that does not exceed 0.06%; at times, an amount of about 0.05%.

In some cases, the wound dressing composition comprises at least trace amounts of the photo-initiator.

In some cases, the wound dressing composition comprises both said at least one photo-initiator and at least one UV cross-linker, wherein the amount of the at least one photo-initiator is up to about 0.1% w/w.

In some cases, the wound dressing disclosed herein contains at least trace amounts of both a photo initiator and a UV cross-linker, the combined amount not exceeding 0.2%.

The hydrogel component of the wound dressing can be formed from different types of hydrogel forming monomers that are cross-linkable by UV irradiation. Typically, when aiming at providing a cross-linked hydrogel by UV irradiation, one would use sulfonate containing monomer units, i.e. the hydrogel is a sulfonate containing hydrogel.

In some examples, the monomer units of the hydrogel are those identified as reactive hydrophilic monomers.

In some examples, the monomer units of the hydrogel are those recognized as forming a medically acceptable hydrogel with water absorbing/swelling capacity.

In some examples, the monomer units of the hydrogel include at least 2-Acrylamido-2-methylpropane sulfonic acid (AMPS).

The hydrogel can be a homopolymer or a copolymer. For example, the hydrogel can be an AMPS homopolymer.

Further, for example, the hydrogel can be a co-polymer. For example, sulfonate containing monomer with vinyl monomers. For example, AMPS is known to react with the following variety of vinyl monomers: acrylic acid, itaconic acid, acrylamide, styrene, vinyl acetate, N-vinylpyrrolidone, 2-hydroxyethyl methacrylate, 2-hydroxypropyl methacrylate, N,N-dimethylacrylamide, N-vinylformamide.

In some examples, the wound dressing also comprises other biopolymers, i.e. other than the cross-linked polymer that formed the hydrogel per se.

In some examples, the wound dressing comprises hyaluronic acid (HA). HA is a polymer known to have, inter alia, anti-bacterial activity. The HA was successfully combined into the honey containing hydrogel to provide a fortified wound dressing. Without being wound by theory, HA (as well as some other polysaccharides such as Carob Gum, a known and commercially available galactomannan polysaccharide) may facilitate/improve absorption of fluids secreted from wounds into the wound dressing. The amount of HA may vary but would typically not exceed 5% out of the total weight of the wound dressing (including water). At times, the amount of HA is in the range between 0.1% to 2% w/w out of the total weight of the wound dressing, at times, in the range of between 0.5% and 1.5% w/w out of the total weight of the wound dressing.

The wound dressing can be characterized by its water or saline holding capacity. This parameter is relevant to the capability of the dressing to absorb extrudates from the wound. In some examples, the wound dressing has an aqueous liquid (saline or water) holding capacity of at least 700 w % from the weight of the dressing before being contacted with liquid material.

The wound dressing disclosed herein may also contain a support matrix, i.e. the combination of the hydrogel and honey are embedded within or onto a support matrix. The support matrix can be a sterile polymer or a sterile fabric. For example, the support matrix can be a polyurethane laminate. If the support matrix is a fabric, it can be a woven or a non-woven fabric.

The wound dressing is prepared by first dissolving the hydrogel forming monomer or monomers with the photo initiator(s) and/or UV cross-linker(s) to form a monomer component and then mixing the same with the honey containing component until a homogenous mixture is obtained. The mixing can be in a homogenizer.

When additional polymers are used, these are typically added to the monomer containing component until all ingredients are uniformly mixed.

The mixture of the components is preferably a homogenous mixture.

For polymerization and hydrogel formation, the mixture is exposed, under controlled conditions to UV irradiation until the mixture solidifies. At times, the mixture is first contacted with the support matrix and only then is exposed to UV light. For example, the support matrix can be soaked with the mixture, the mixture can be brushed or sprayed over the support matrix etc.

When referring to UV irradiation under controlled conditions it is to be understood as the conditions sufficient for cross-linking to take place. The conditions are dictated by the type and/or concentration of any one of the monomer(s) used, photo-initiator(s), UV cross-linker(s), honey, additional polymers.

In some examples, the curing/polymerization involves exposure to the UV light is by the use of a 230V/50 Hz, 400 W Mercury lamp. The exposure time may vary, and yet would typically be a matter of from milliseconds to several seconds.

Mercury UV lamp output is mainly in UVC spectrum. This was sufficient to provide effective curing. The conditions of use including the output of Mercury UV lamp for various UV wavelengths is available in the lamp manufacturer's specifications.

Once prepared, the wound dressing can then be stored within dedicated packages, typically, sterile packages.

Upon need, the wound dressing is used for treating a wound. In this context, treating should be understood as encompassing also preventative/prophylactic treatment, i.e. for the prevention of an undesired condition from occurring.

In some examples, the wound dressing is used for treating a wound that has been diagnosed as being infected with a bacterial infection. In some other examples, the wound dressing is used for treating a wound that while not yet being identified as having an infection, is in predisposition of developing an infection.

Without being limited thereto, the wound dressing disclosed herein can be used for treating open wounds, surgical wounds, bedsores, insect bites and secondary inflammation due to skin diseases. In one specific example, the wound dressing is for use with surgical In some cases, the wound dressing is used for application onto surgical sites to treat or prevent post operational complications such as surgical site infections (SSI).

Treatment of the wound may include periodical replacement of the wound with a fresh wound dressing. The frequency of replacement will be dictated by the time of wound being treatment, the condition of the wound being treated, the composition of ingredients forming the wound dressing, as well as any other consideration commonly taken by the physician.

Non-Limiting Examples

Preparation of a Wound Dressing Composition
Materials
Monomers:
2-Acrylamido-2-methylpropane sulfonic acid, sodium salt (AMPS) manufactured by Lubrizol Chemical company, in particular AMPS 2408A including 58% w/w of the monomer dissolved in water, CAS number 15214-89-8.

Hyaluronic Acid, Sodium Salt from synthetic source (HA) with molecular weight of circa 1,420,000 Da and chemical cleanness of above 93%, manufactured by Xi'an Pincredit Bio-tech Co., Ltd, CAS number 9067-32-7

Clarified Carob (Locust Bean) Gum cosmetics grade manufactured by CP Kelco, CAS number 9000-40-2

High acyl Gellan Gum ($1-2 \times 10^6$ Daltons) cosmetics grade, manufactured by CP Kelco, CAS number 71010-52-1

Methylcellulose (Methocel A40M) food grade modified cellulose manufactured by Dow, Cas number 9004-67-5

Xanthan gum (KELTROL Advanced Performance xanthan gum, cosmetic grade) manufactured by CP Kelco, Huber Company CAS number 11138-66-2

Photo-Initiators:
2-Hydroxy-2-methylpropiophenone (GENOCURE DMHA) manufactured by RAHN Group, Switzerland, CAS number 7473-98-5, as a low pressure photo-initiator.

Ethyl (2,4,6-trimethylbenzoyl) phenyl phosphinate (GENOCURE TPO-L) manufactured by RAHN Group, Switzerland, CAS number 4434-11-7 as a medium pressure photo-initiator.

Diphenyl(2,4,6-trimethylbenzoyl) phosphine oxide 10%-25% (GENOCURE LTM) manufactured by RAHN Group, Switzerland, CAS number 75980-60-8 as broad spectrum photoinitiator Specially treated Medicinal Honey, manufactured by LMesitran, CAS number 8028-66-8 as a broad spectrum photoinitiator Crosslinkers Ethylene Glycol Dimethacrylate manufactured by Merck, CAS number 25852-47-5

Polyethylene glycol (400) diacrylate (Miramer M280) manufactured by RAHN Group, Switzerland, CAS No. 26570-48-9

4-(1-Oxo-2-propenyl)-morpholin (Genocure ACMO) manufactured by RAHN Group, Switzerland, CAS number 5117-12-4

Actives

Hyaluronic Acid, Sodium Salt as a superabsorbent.

L-Mesitran® Medicinal Honey as an antibacterial agent.

Other Components 1,2,3-Propanetriol (Glycerol) by various manufacturers, CAS number 56-81-5 as a solvent Purified water as a solvent.

Methods and Results

Determination of optimal honey content in hydrogel

Honey optimal content, affecting the curing process, has been predetermined by viscosity measurement (AMPS added to 100% content), as described in Table 1 below.

All components of the various tested mixtures were combined together and homogenized until uniform and clear. Then the mixtures were exposed to UV for 1 second (see Section "Curing (polymerization) of hydrogel protocol" for details) to form the cross-linked hydrogels. These hydrogels samples were collected, and their viscosity was measured.

Low viscosities of less than 1000 cPs were measured using "Cannon-Fenske" opaque viscosimeters manufactured by Connecta (see in this connection Viscosity Measurement Using CANNON-FENSKE Viscometers as described by Tianguang Fan (Oct. 26, 2001) http://www.prrc.nmt.edu/groups/petrophysics/media/pdf/viscometer.pdf).

Viscosities of higher than 1000 cPs were measured using MYR VR-3000 Brookfield-type viscometer with following spindles:

Spindle R2 at 12 rpm for viscosities between 1,000 and 3,333 cPs;

Spindle R3 at 12 rpm for viscosities between 3,333 and 8,333 cPs;

Spindle R5 at 12 rpm for viscosities between 8,333 and 33,333 cPs;

Spindle R7 at 12 rpm for viscosities between 33,333 cPs and 333,333 cPs.

For high viscosities, when liquid still behaves as Newtonian, viscosities were checked at various shear rates and averaged. When behavior became non-Newtonian viscosities over a range of viscosities at high shear rates (when viscosities do not change significantly) were averaged.

Generally, the transition from Newtonian to non-Newtonian behavior in hydrogel systems occur between about 1000 mPas and 10,000 mPas. At this range the viscosity behavior can still be regarded as Newtonian. Table 1A provides the viscosity of a formulation comprising 10% honey, 0.15% linkers and no initiators.

TABLE 1A

Viscosity as a function of shear rate
10% honey, 0.15% linkers, 0% initiators

| Shear Rate, rpm | Viscosity mPas |
|---|---|
| 2 | 4400 |
| 2.5 | 4350 |
| 3 | 4300 |
| 4 | 4230 |
| 5 | 4160 |
| 6 | 4120 |
| 8 | 4090 |
| 10 | 4060 |
| 12 | 4060 |

At non-Newtonian behavior, the deviation from the average viscosity increases dramatically with the increase of the shear rate. Thus, at viscosities which are higher than 10,000 mPas, the viscosity should be averaged over the results of higher shear rates. Table 1B provides the viscosity of a formulation comprising 10% honey, yet no linkers and 0.05% initiators. The behavior was non-Newtonian.

TABLE 1B viscosity as a function of shear rate
10% honey, 0% linkers, 0.05% initiators

| Shear Rate, rpm | Viscosity mPas |
|---|---|
| 2 | 60200 |
| 2.5 | 52000 |
| 3 | 47200 |
| 4 | 40100 |
| 5 | 34700 |
| 6 | 31200 |
| 8 | 29500 |
| 10 | 28900 |
| 12 | 27800 |

Without being bound by theory, it is considered that the increased viscosity should testify to initiation of the polymerization process. The higher viscosity is indicative of a higher degree of polymerization. However, at a certain stage of polymerization, the hydrogel developed visco-elasticity and shear thinning behavior and became rigid (viscosity became infinitively high (not shown in Table 1B)). Thus, the steady viscosity test was used for indication of the polymerization process only.

The results of viscosity measurements used for initial adjustment of hydrogel formulation comprising a fixed amount of the monomer AMPS and HA (53.15% of AMPS and 1% of HA, indicated amounts of honey, linkers and initiators (and filled to 100% with process water) are provided in a Table 1C.

TABLE 1C

Viscosity of mixtures of various compositions
including the monomer AMPS

| Raw Material | LMesitran Medicinal Honey | Total photo-initiators | Total cross-linkers | Viscosity, cPs |
|---|---|---|---|---|
| Concentration % w/w | 0 | 0 | 0 | 15 |
| | 0 | 0.05 | 0 | |
| | 0 | 0 | 0.15 | |
| | 0 | 0.1 | 0.7 | 4,000 |
| | 0 | 0.2 | 0.7 | Inf. |
| | 5 | 0 | 0 | 18 |
| | 5 | 0.05 | 0 | 100 |

TABLE 1C-continued

Viscosity of mixtures of various compositions including the monomer AMPS

| Raw Material | LMesitran Medicinal Honey | Total photo-initiators | Total cross-linkers | Viscosity, cPs |
|---|---|---|---|---|
| | 5 | 0 | 0.15 | 35 |
| | 10 | 0 | 0 | 20 |
| | 10 | 0.05 | 0 | 30,000 |
| | 10 | 0 | 0.15 | 4,200 |
| | 10 | 0.05 | 0.15 | Inf. |
| | 20 | 0 | 0 | 76 |
| | 20 | 0.05 | 0 | Inf. |
| | 20 | 0 | 0.15 | 7,500 |
| | 20 | 0.01 | 0.15 | 12,000 |
| | 20 | 0.02 | 0.15 | 19,000 |
| | 20 | 0.03 | 0.15 | 29,000 |
| | 20 | 0.04 | 0.15 | 46,000 |
| | 20 | 0.05 | 0.15 | Inf. |

Table 1C shows that honey can partially replace photo-initiators and/or cross-linkers. At honey concentration of 5% the effect was negligible (viscosity of the mixture including 0.05% of initiator, 0% of linker and 5% of honey was increased from 18 cPs to 100 cPs). At 10% and 20% of honey the polymerization process was more pronounced. Hydrogel containing 20% honey was preferable due to its better therapeutic properties (see below). In all formulations it is shown that the combined amount of initiator and cross linker could be equal or less than 0.2% w/w in order to allow sufficient solidification in the presence of honey. This is specifically unique in view of the much higher amount of these agents required for the same solidification in the absence of honey ("0" honey).

Honey Selection

In order to better understand honey mechanism of action, two types of honey (L-Mesitran light honey and Avocado dark honey) were examined a part of the monomer mixture and viscosity of each mixture was checked.

Specifically, honey was added to the monomer mixture at room temperature or under heating at 50° C. In the case of heating, the mixture was maintained at 50° C. only while mixing until uniformity. No photo-initiators or cross-linkers were added to each mixture.

Viscosities were determined when the temperatures of each mixture reached 25° C. Before adding the honey, viscosity of each mixture was 10-11 cPs (the base line, before curing). The viscosities after curing with honey (but without any initiator or cross-linker) are provided in Table 2.

TABLE 2

Viscosities of mixtures including honey and monomer (AMPS)

| | Viscosity, cPs | |
|---|---|---|
| Honey type and content | Cold mixing | Mixing at 50° C. |
| 10% L-Mesitran Medicinal Honey | 20 | 15 |
| 20% L-Mesitran Medicinal Honey | 76 | 18 |
| 10% Avocado Honey | 50 | 35 |
| 20% Avocado Honey | 85 | 35 |

Table 2 shows that the viscosity of the mixtures including Avocado honey was higher than that of the mixtures containing L-Mesitran Medicinal honey. Yet, when mixed at 50° C., the increase in honey concentration did not affect the resulting viscosity. It is assumed that the difference in viscosities resides in the fact that avocado honey contains metal ion (absent from the medical honey) and these ions induce the monomer (AMPS) cross-linking/polymerization process at the high temperatures i.e. at 50° C., even in the absence of cross-linkers or initiators, and yet at which free radicals are no longer formed by the honey. As a result, the only polymerization process that takes place is that induced by the metal ions.

The results also show that in the medicinal honey, where there is no or low metal ion content, the level of cross-linking under cold conditions is greater at 20% honey. This may be explained by the inhibitory effect of heating on the production of $H_2O_2$ by the enzymes in the honey, thus also reducing the cross-linking level under heating. In other words, it appears that the heating has a dual damaging effect, on the one hand, reducing cross lining, and on the other hand, reduces the activity of the enzymes residing in the honey. The above results suggested working with 20% honey in the following experiments.

Table 3 represents viscosities of hydrogel mixtures, prepared with avocado honey when mixed at room temperature (RT) or at 50° C.

TABLE 3

Viscosities of cross-linked hydrogel of various compositions containing Avocado honey (dark Avocado) including monomer

| Raw material | Avocado Honey | Total photo-initiators | Total cross-linkers | Viscosity, cPs (RT) | Viscosity, cPs (50°C) |
|---|---|---|---|---|---|
| Concentration % w/w | 0 | 0 | 0 | 15 | 30 |
| | 0 | 0.05 | 0 | | |
| | 0 | 0 | 0.15 | | |
| | 5 | 0 | 0 | 21 | 35 |
| | 5 | 0.05 | 0 | 5,000 | 70 |
| | 5 | 0 | 0.15 | 40 | 95 |
| | 10 | 0 | 0 | 50 | 35 |
| | 10 | 0.05 | 0 | Inf. | 4,500 |
| | 10 | 0 | 0.15 | 3,500 | 2,800 |
| | 10 | 0.05 | 0.15 | Inf. | Inf. |
| | 20 | 0 | 0 | 85 | 35 |
| | 20 | 0.05 | 0 | Inf. | Inf. |
| | 20 | 0 | 0.15 | 8,000 | 4,000 |
| | 20 | 0.05 | 0.15 | Inf. | Inf. |

Table 3 shows that in the absence of honey, the cross linking and hydrogel formation is low (low viscosity) and yet, in the presence of the honey, even in the presence of metal ions (present in dark honey), there is cross linking. Interestingly, at the same concentration of cross linkers, the heating reduced the contribution of the enzymes to the cross-linking process. This may be due to effect of heating on the enzymes inherently present in the honey, i.e. probably because the heating damaged the functionality/activity of the enzymes inherently within the honey.

Protocol for Determining Peroxide Content in Honey Mixture

The purpose of this assay is to determine the amount of peroxide formed in the mixtures. The higher the content, the greater the antimicrobial activity of the honey containing formulation. The peroxide is formed by the enzymatic activity within the honey. It is desired that the enzymes are not damaged, e.g. by heating that typically takes placed in thermal polymerization.

Protocol:
Take 50 g of hydrogel mixture (can also be a rigid hydrogel);
Add 40 gr of water and mix until uniform or in case of using a rigid hydrogel wait until water is fully absorbed;
Incubate at 30° C. for 1 hr;
Check the solution/gel has a pH value of 2-12. If no, adjust pH using sodium hydroxide or citric acid.
Take one strip of QUANTOFIX® Peroxide 25
Dip the test strip into the test solution for 1 s.
Shake off excess liquid/gel.
Wait 15 seconds.
Compare with the color scale. If hydrogen peroxide is present, the test field turns blue.

Results:
Hydrogen peroxide content after 1 hr incubation at 30° C. is provided in Table 4. The compositions tested in this respect included 0.05% photo-initiator, 0.15% linker, 53.15% AMPS, 1% HA, and honey as specified, water was added to 100%.

TABLE 4

$H_2O_2$ release from different compositions (average of triplicate)

| Specification | Result | | | | | | |
|---|---|---|---|---|---|---|---|
| Avocado Honey, % | 0 | 5 | 10 | 20 | 0 | 0 | 0 |
| Acacia Honey, % | 0 | 0 | 0 | 0 | 5 | 10 | 20 |
| $H_2O_2$ production (RT), mg/L | 0 | 0-0.5 | 5-10 | 5-10 | 0-0.5 | 2-5 | 5-10 |
| $H_2O_2$ production (50° C.), mg/L | 0 | 0 | 0 | 0-0.5 | 0 | 0 | 0 |

The results show that at 10% Acacia honey there is already good production of 2-5 room temperature and at same concentration, yet at 50° C. there is no peroxide production, this indicating that enzymatic activity required for peroxide production, has been damaged by the heating.

The results also show that both dark honey and light honey have better $H_2O_2$ production at room temperature, the activity resulting from the enzymatic activity that is damaged upon heating.

Notably, the results show that peroxide release does not require presence of polymerization initiators or linkers and depends only on the presence of honey.

Hydrogel-Hyaluronic Acid (HA) Preparation

The end formulation comprises also hyaluronic acid (HA) so as to facilitate/improve absorption of any fluids secreted from the wound. To this end, the following preparation protocol took place:

PREMIX I: Disperse 3% of HA in water. Wait circa 24 hours until fully dissolved and uniform. Add L-Mesitran Medicinal Honey, mix until uniform.

PREMIX II: Add AMPS to the main mixing reactor. Add photo-initiators and crosslinkers and homogenize until uniform and clear. Make sure that no oily spots appear on the PREMIX II surface.

Gradually add PREMIX I to PREMIX II under mixing. Homogenize until uniform. Leave under slow mixing and protected from UV light till fed to curing station (to avoid undesired cross linking-before time).

Subject to UV light for curing, as described below.

According to the above protocol, eight hydrogel compositions were prepared for analysis. Compositions 1-8 are provided in Table 5.

The metal content in honey ranges from 0.04% in light honeys to 0.2% in dark honeys [Oryan et al. 2016]. L-Mesitran Acacia Medicinal honey was chosen for various reasons, including its low content of minerals and metal ions, thus assumed to have better antimicrobial activity as well as for its lower bioburden relative to dark honey (thus making the sterilization process more feasible).

TABLE 5

Hydrogel-HA Compositions

| | Concentration in Composition No. (% w/w) | | | | | | | |
|---|---|---|---|---|---|---|---|---|
| Component | 1 | 2 | 3 | 4 | 5 | 6 | 7 | 8 |
| AMPS monomer | 100 | 53.15 | 53.15 | 53.15 | 53.15 | 53.15 | 53.15 | 53.15 |
| L-Mesitran Medicinal Honey | 0 | 20 | 20 | 20 | 0 | 20 | 5 | 10 |
| Total photo-initiators | 0 | 0 | 0 | 0.05 | 0.05 | 0.05 | 0.05 | 0.05 |
| Water | 0 | 25.85 | 25.7 | 25.8 | 46.65 | 25.65 | 40.8 | 35.8 |
| Hyaluronic Acid | 0 | 1 | 1 | 1 | 1 | 1 | 1 | 1 |
| Total cross-linkers | 0 | 0 | 0.15 | 0 | 0.15 | 0.15 | 0 | 0 |

Compositions 4, 5 and 6 included the same amount of photo-initiators. Compositions 3, 5 and 6 include same amount of cross-linkers.

Composition 6 represents the final/preferred composition. Composition 3 differs from composition 6 in the photo-initiators being replaced with water in (i.e. no photoinitiator in composition 3). Composition 4 differs from composition 6, with the cross-linkers being replaced by water (i.e. no cross-linker in composition 4). Composition 5 differs from composition 6, in that Lmesitran Medicinal Honey is replaced with water. Composition 2 differs from composition 6 in that it contains no cross-linkers or photo-initiators. Compositions 7 and 8 differ from composition 4, with honey, partially replaced by water.

UV Curing (Polymerization) of Hydrogel

The hydrogel was distributed over base material surface, such that the gel depth/thickness over the surface was between 0.9 and 1.3 mm. The gel was then covered by a Non-Woven material having a density of 13 gram per square meter weight to prevent surface tension driven flow and change in the gel depth. Curing was performed by exposure, for about 1 second, to a 230V/50 Hz, 400 W Mercury lamp (manufactured by Hoenle group, Germany). The output of Mercury UV lamp for various UV wavelengths is available in the manufacturer specifications.

Mercury UV lamp output is mainly in UVC spectrum. This was sufficient to provide effective curing.

Determining Curing Level

The compositions detailed in Table 4 were tested for monomer content (namely, level of cross-linking) using two independent techniques: thermogravimetric analysis [Golon and Kuhnert, 2013; Simkovic et al., 2003] and Flory-Rehner method [Durmaza and Okay, 2000] as described below.

Thermogravimetric Analysis (TGA)

Thermal decomposition analysis was performed on the hydrogel compositions in order to determine monomer content in each hydrogel composition (i.e. level of curing). Thermal decomposition of the hydrogels was observed in terms of global mass loss using SDTQ600 TGA instrument.

Samples of 10 mg were evenly and loosely distributed in an open pan made of alumina and introduced into a micro-furnace. The heating rate was 5° C./min. The temperature change was controlled from room temperature (25° C.) to final temperature of 200° C. The weight loss, heating time and sample temperature were continuously recorded during the test.

Decomposition temperatures were found based on differential thermogravimetric analysis (DTG) of TGA instrument software and fixed at extremum points of DTG data. Lower and upper limits of a certain decomposition temperature are DTG curve inflection points, closest to the extremum (decomposition) point of DTG, or limits of test area (RT or 200° C.).

For correct analysis of the hydrogel samples, main raw materials (monomers and LMesitran Medicinal Honey) were analyzed prior to test so as to verify their temperature of decomposition.

FIGS. 1A-1B, 2A-2B and 3A-3B represent results of TGA (TG and DTG) for the raw material LMesitran Medicinal Honey, Hyaluronic Acid (HA), and AMPS, respectively. The Data from the TGA analysis is also summarized in Table 5 below.

Figure 1B:
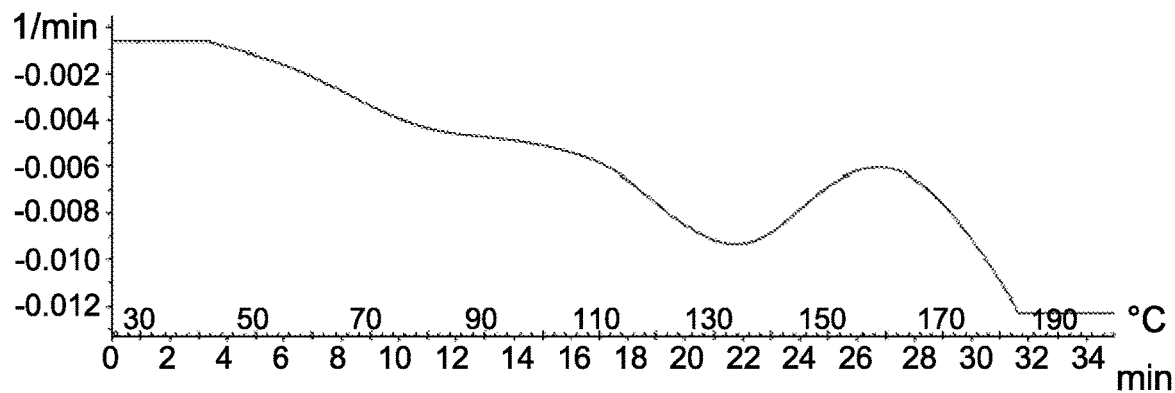

Specifically, FIGS. 1A-1B show that LMesitran Medicinal honey includes three main elements: a first element that decomposed at about 90° C. and presumably is water (the sample was not dried out prior the test to prevent sugar decomposition), the second element decomposed at about 130° C. and presumably is fructose [A Golon, (2013). ibid], and the third element decomposed at about 190° C. and presumably is sucrose [I Simkovic, et al. 2003 ibid].

The exact decomposition points were not evident in the TG analysis. As appreciated, chemically clean substances decompose at exact certain temperatures. However, honey decomposed at temperature ranges probably due to some impurities or due to the natural origin of LMesitran Medicinal Honey including a combination of organic matter, such as beeswax, plant parts, bees' and other insect tissues, pesticides, and others. In addition, some natural monosaccharides continuously degrade at high temperatures to form other types of sugars with different characteristics, for example, decomposition of fructose to lactose. However, the decomposition points could be detected from the DTG results.

Figure 2A:
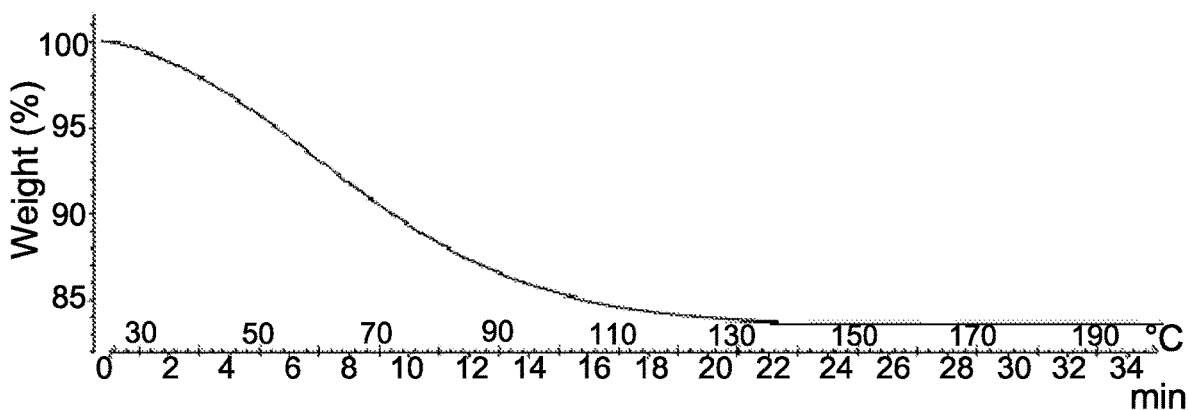
FIGS. 2A-2B provide TGA results of Hyaluronic Acid where FIG. 2A provides TG, i.e. the % weight (weight %) of Hyaluronic Acid versus temperature (C) and FIG. 2B provides DTG of Hyaluronic Acid versus temperature (° C.); both Figures being at a heating rate of 5° C./min.
Figure 2B:
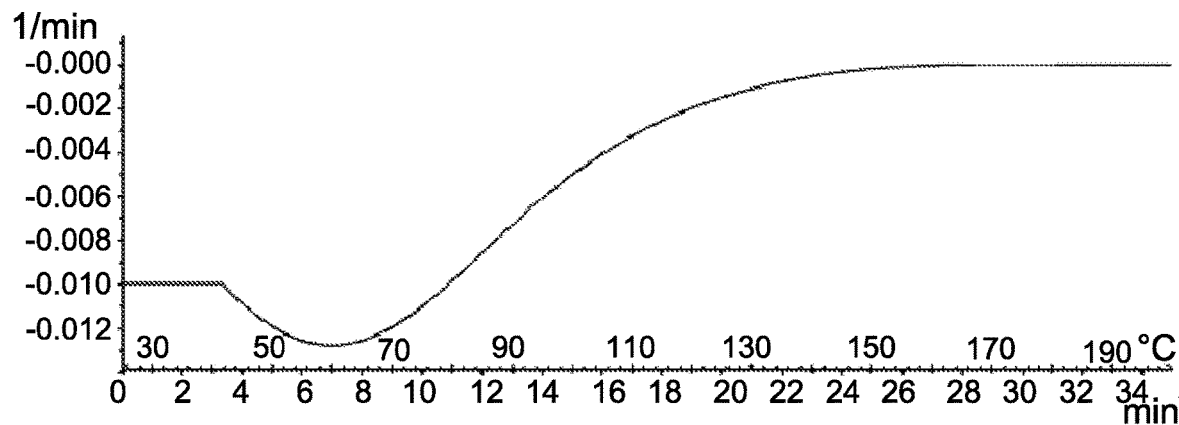

The decomposition of HA was also gradual, as shown in FIGS. 2A-2B. This was despite the synthetic origin and relative chemical purity which should have provided a relatively narrow temperature range at which the HA decomposes. The gradual decomposition could be due to the high hygroscopicity of HA, resulting in relatively high water content even in dried samples.

Figure 3A:
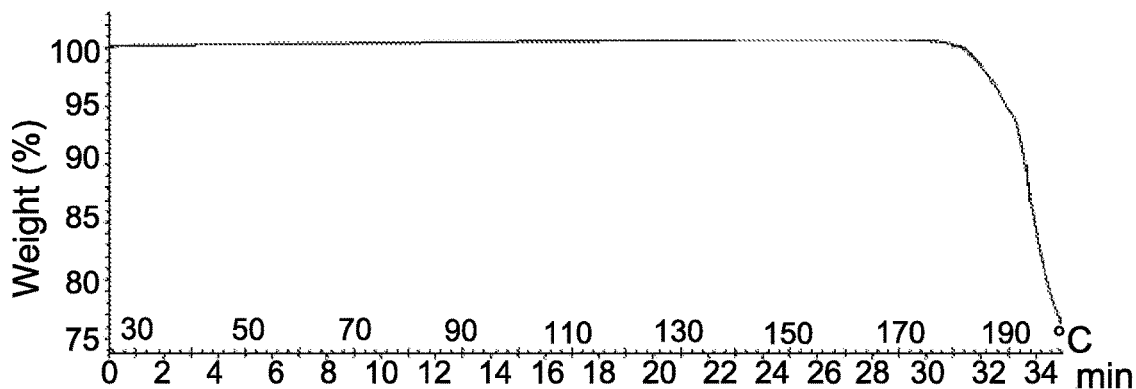
FIGS. 3A-3B provide TGA results of AMPS where FIG. 3A provides TG, i.e. the % weight (weight %) of AMPS versus temperature (° C.) and FIG. 3B provides DTG, i.e. % weight change in time (%/min) of AMPS versus temperature (° C.); both Figures being at a heating rate of 5° C./min.
Figure 3B:
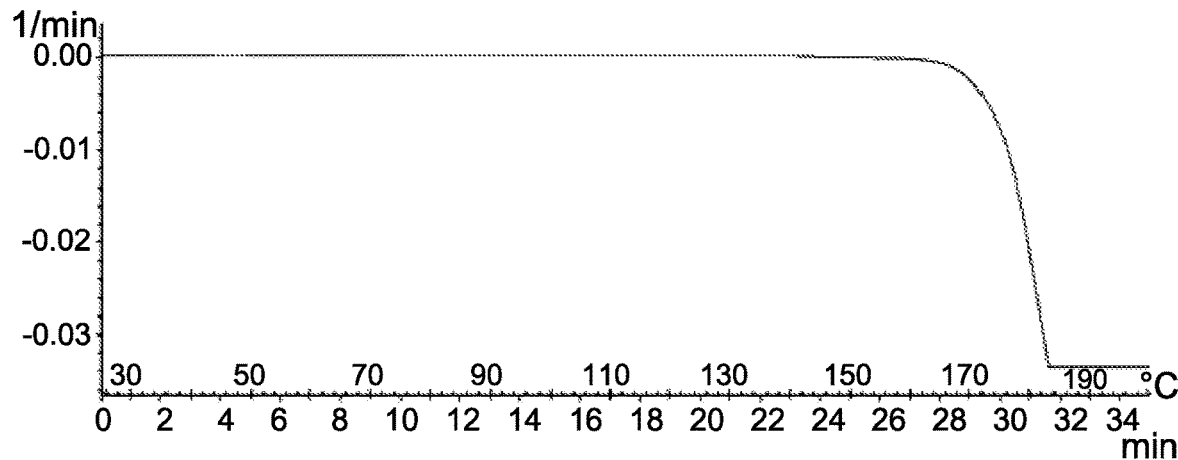

The decomposition point of AMPS monomer was determined with relatively high accuracy from FIGS. 3A-3B.

Table 6 summarizes decomposition temperatures and elements that possibly decomposed at these decomposition temperatures.

TABLE 6

Honey, HA and AMPS content and decomposition temperatures based on TGA analysis

| Material | Decomposition temperature, ° C. | | | | % decomposition at heating rate of 5° C./min | % of element based on specs |
|---|---|---|---|---|---|---|
| | Nominal | Lower limit | Upper limit | Element | | |
| Honey | 88 | 42 | 109 | water | 4.76 | <20 |
| | 134 | 109 | 163 | fructose | 8.31 | 35-40 |
| | 188 | 162 | 199 | glucose | 8.66 | 25-30 |
| HA | 65 | RT | 199 | HA | 16.43 | >93 |
| AMPS | 168 | 164 | 197 | AMPS | 24.55 | >99 |

In addition, TGA of compositions 2-6 at temperature range between 164° C. and 199° C. was also determined and the results are shown, respectively, in FIGS. 4A-4E.

Figure 4A:
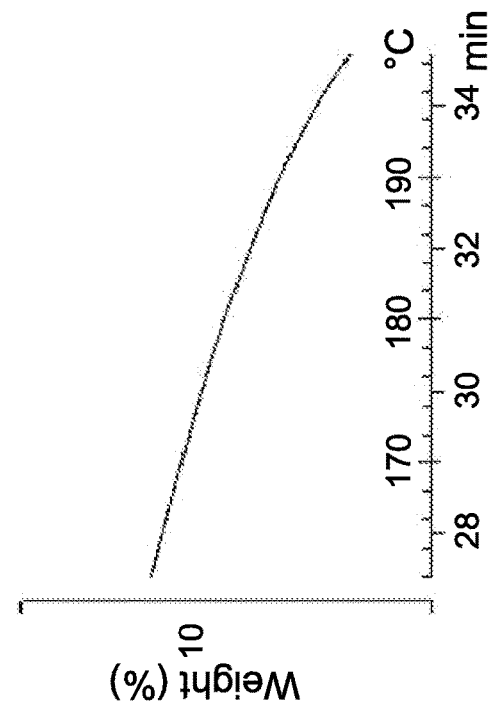
FIGS. 4A-4E provide TGA (% weight (% weight) vs. T (° C.)) analysis results for samples from composition #2 (FIG. 4A), composition #3 (FIG. 4B), composition #4 (FIG. 4C) composition #5 (FIG. 4D); and composition #6 (FIG. 4E), all being at a heating rate of 5° C./min.
Figure 4B:
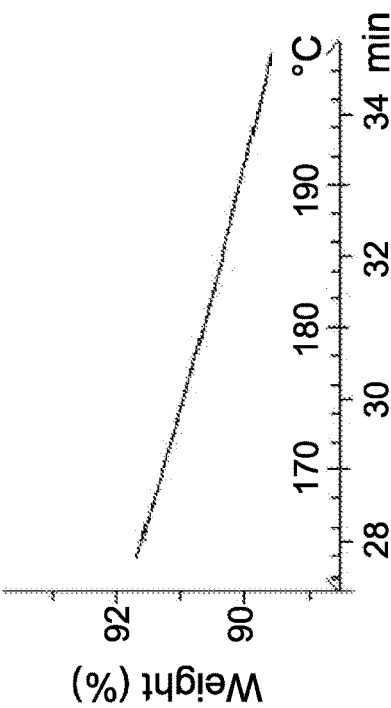
Figure 4C:
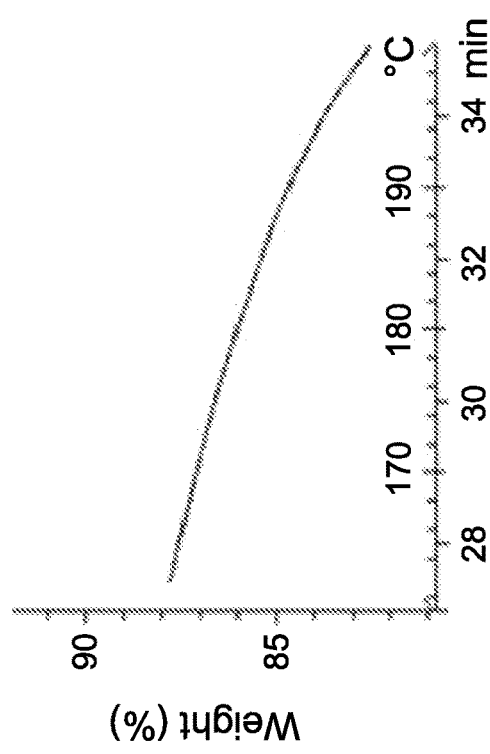
Figure 4D:
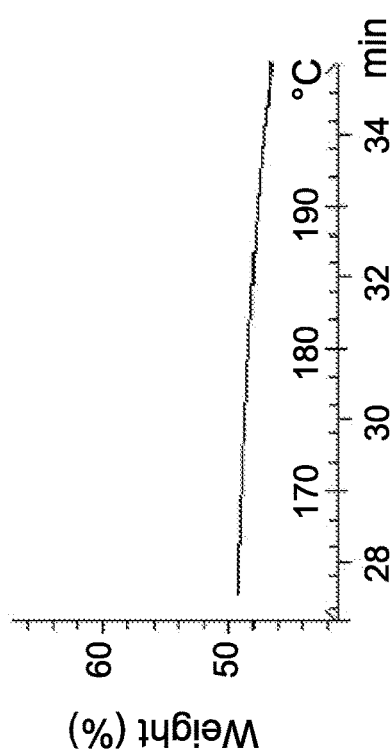
Figure 4E:
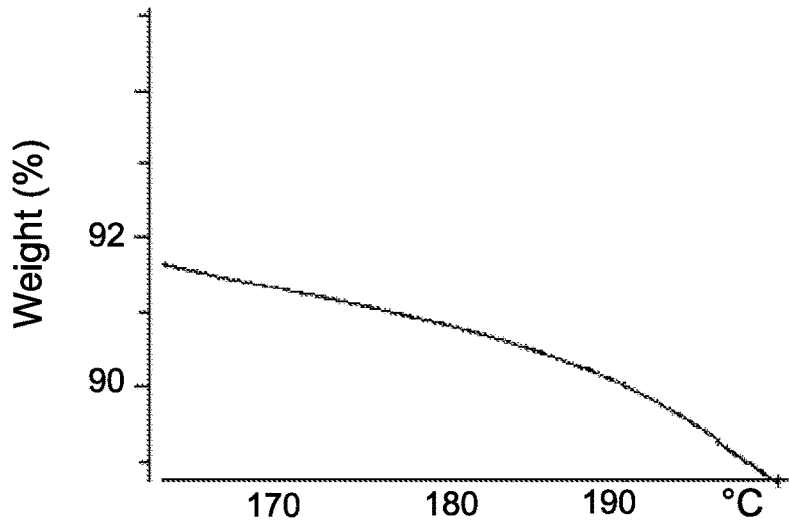
Figure 5:
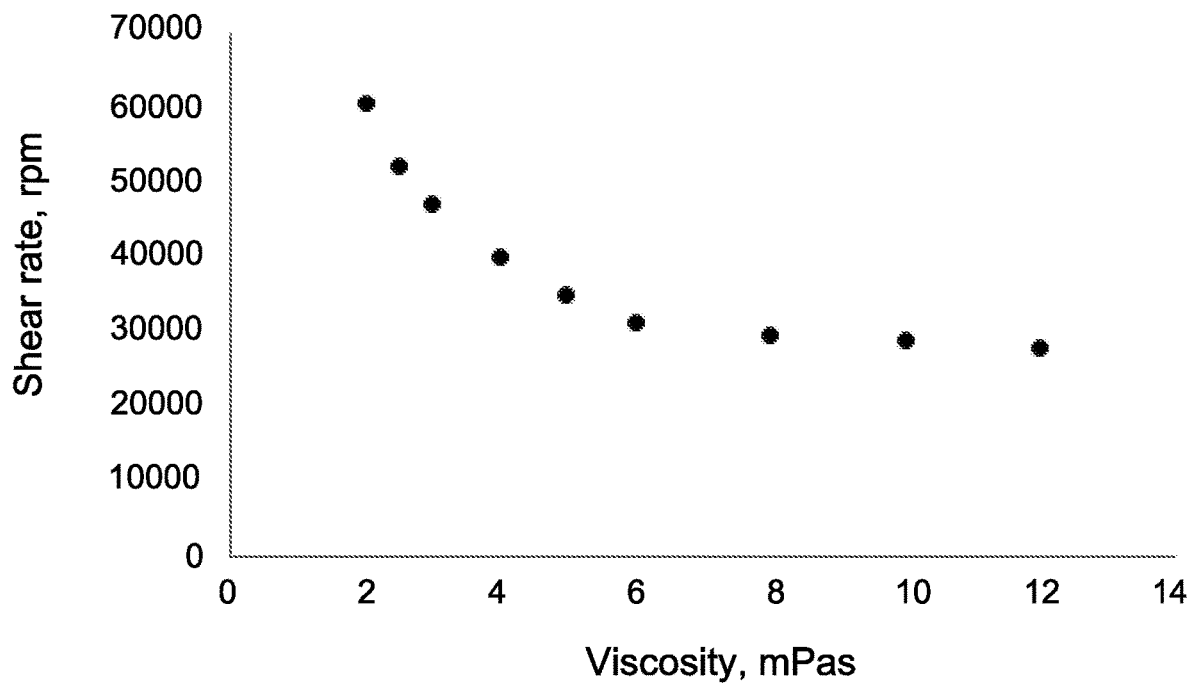
FIG. 5 provides a graph showing viscosity of hydrogel containing honey (see composition #8 in Table 5) at various shear rates.

The decomposition temperature as estimated based on DTG analysis was 186° C. for compositions 2 and 3 (FIGS. 4A and 4B, respectively), 188° C. for composition 4 (FIG. 4C), 190° C. for composition 5 and 6 (FIGS. 4D and 4E, respectively). These small differences can be considered within the range of standard experimental errors, and/or result from impurities in the compositions etc.

At heat rate of 5° C./min 23.8806% of dry AMPS monomer sample disintegrates at temperatures between 164° C. and 199° C. (see FIGS. 3A-3B). Compositions 2-6 include 30.83% AMPS dry monomer and thus mass reduction of compositions 2-6 before curing due to AMPS was expected to be 7.36%. Under the same experimental conditions LMesitran Medicinal Honey lost 8.6612% of its weight at temperatures between 163° C. and 199° C. Thus, when 20% of LMesitran Medicinal Honey was added to the formulation (compositions 2, 3, 4) additional weight reduction of circa 1.73% was expected in samples of these compositions before curing. Under the assumption that change in concentration of honey due to the curing is negligible, concentration of AMPS monomer in the hydrogel sample after curing was determined as following:

$$C_{AMPS,i} = \frac{c_i - i_H c_{H,0}}{c_{AMPS,0}} 100\%, \quad (1)$$

in which $C_{AMPS,i}$ is concentration of AMPS monomer in sample i after curing; i=2,3,4,5 is the composition # as described in Table 4; $C_i$ is percentage of weight reduction of composition i at temperatures between 164° C. and 199° C.; $i_H$ (0.2 (20%) for compositions 2,3,4, and 0 for composition 5) is a fraction of LMesitran Medicinal Honey in composition i before curing; $C_{H,0}$ is weight reduction in LMesitran Medicinal Honey sample (see FIG. 1 for details); $C_{AMPS,0}$ is weight reduction in AMPS monomer sample (see FIG. 4); $i_{AMPS}$=0.3083 (for all composition) is a fraction of AMPS monomer in composition i before curing. 10 TGA results of compositions 2-6 at temperature range between 164° C. and 199° C. was determined and the results are shown in Table 7.

TABLE 7

Composition and concentration of monomer after polymerization, based on TGA analysis

| Parameter | Sample | | | | |
|---|---|---|---|---|---|
| | 2 | 3 | 4 | 5 | 6 |
| Weight reduction between 164° C. and 199° C., % w/w | 5.362 | 5.2834 | 2.6834 | 1.0788 | 1.699 |
| Concentration of AMPS monomer (TGA result) in hydrogel, % w/w | 15.2 | 14.9 | 4.0 | 4.5 | 0 |

As seen, about 50% w/w of monomer polymerized when no photo-initiator was added to the composition (reduction from 30.83% to 15.2% of monomer in composition 2 and to 14.9% in composition 3). When 0.15% of cross-linkers was added to the composition, content of AMPS monomer reduced from 15.2% in composition 2 to 14.9% in composition 3, thus initiator can at least partially be replaced with Honey. When 0.05% of photo-initiator is added, concentration of AMPS monomer reduces from 15.2% in compositions 2 to 4 and null (0%) in composition 4. When no honey was added to the formula, but 0.15% of chemical linkers and 0.05% of chemical initiators were used, concentration of monomer was higher than in the formula including 0.05% of chemical initiators and no chemical linkers, i.e. concentration of monomer in compositions 5 is 4.5, while in composition 4 it was only 4.0%. Thus, chemical linkers can be replaced in full by LMesitran Medicinal Honey, which can be even more effective than chemical linkers.

With respect to composition 6 it is noted that the expected reduction of sample weight due to honey presence was 1.73%, while the actual result was 1.699% weight reduction. This small difference could be due to experimental error Flory-Rehner Method In order to determine monomer content in hydrogel using Flory-Rehner method, the test samples were dried out to less than 1% humidity prior the testing. To reduce a risk of monomer evaporation the compositions were dried out at 40° C. Specifically, samples of 100 gr were dried out for 10 days in a 40° C. incubator, cooled for 12 hours to room temperature in a desiccator and weighted. After weighting the samples were incubated again at 40° C. The weight of the samples was checked every 5 days (day 15, 20, 25, etc.). The samples were ready for the following tests if weight difference between two consequent tests (day 15 and day 10, or day 20 and day 15, etc.) was within the accuracy of the scales. The drying time can vary as a function of weather, water content in LMesitran Medicinal Honey and other parameters. In most cases drying time was 15 days (but can reach 20 and even 25 days).

Samples of the dry hydrogel compositions (100 gr) were placed to a vessel including 1 L of purified water at room temperature and mixed for 25 minutes. Then water was replaced with fresh 1 L of purified water and mixed for other 25 minutes. After the procedure the samples we dried out, weighted and washed and dried again. The procedure was repeated until the weight of the dry sample stopped changing.

Under these conditions HA monomers can fully evaporate and honey can fully dissolve from the hydrogel together with the monomers. These possible effects are to be taken into account while analyzing the test results.

Samples were weight before and after drying, and monomer concentration in dried formula, before curing were estimated, the results are given in Table 8.

In Table 8, the estimated content (grams) is the concentration of the element in the composition before curing multiplied by content according to manufacturer's specifications (30.83% for AMPS and 0.93% for HA) and by the sample weight. The concentration was estimated before curing relatively to the dry sample weight. Honey, used for the study, was dried out at 40° C. until the weight stopped changing, and water content in the honey batch was 9%.

The concentration of AMPS monomer in wet samples was equal to 53.15% of AMPS 2405A (as detailed in Table 4), or 30.83% of dry AMPS monomer before curing. The concentration of HA monomer in wet samples was equal to 1% of HA (as detailed in Table 4), or above 0.93% of dry HA before curing.

TABLE 8

Dry samples composition (2 to 8)

| Characteristic | Composition | | | | | | |
|---|---|---|---|---|---|---|---|
| | 2 | 3 | 4 | 5 | 6 | 7 | 8 |
| Weight before drying, W, gr | 101.2 | 99.8 | 105.1 | 100.4 | 103.6 | 100.0 | 98.4 |
| Dry sample weight, $W_d$, gr | 49.9 | 49.3 | 51.9 | 31.7 | 51.3 | 36.3 | 40.2 |

TABLE 8-continued

Dry samples composition (2 to 8)

| Characteristic | Composition | | | | | | |
|---|---|---|---|---|---|---|---|
| | 2 | 3 | 4 | 5 | 6 | 7 | 8 |
| AMPS monomer content before curing as dry residual, $W_{AMPS, r}$, gr | 31.2 | 30.8 | 32.4 | 31.0 | 31.9 | 30.8 | 30.3 |
| AMPS estimated concentration, % (based on dry residual) | 62.5 | 62.5 | 62.4 | 97.8 | 62.2 | 84.9 | 76.7 |
| HA estimated content, gr | 0.94 | 0.93 | 0.98 | 0.93 | 0.96 | 0.93 | 0.92 |
| HA estd. concentration, % (based on dry residual) | 1.9 | 1.9 | 1.8 | 2.9 | 1.9 | 2.5 | 2.3 |
| Honey content as dry residual, $W_H$, gr | 18.2 | 18.2 | 18.2 | 0 | 18.2 | 4.55 | 9.1 |

Note that total estimated (theoretical) content of AMPS and HA together in composition 5 was (97.8+2.9=100.7%), namely at least 24.7%, which is 0.23 gr of 0.93 gr of HA evaporated while drying. This is based on the worst-case estimation, and according to the above, the photo-initiators and cross-linkers fully evaporate during drying and AMPS did not evaporate due to the relatively high decomposition temperature (decomposition temperature is between 164° C. and 197° C., while drying temperature was 40° C.

The samples as described in Table 5 were washed and dried out 3 to 5 times according to the procedure described above. Monomer content in the samples was estimated as following:

$$W_{AMPS,m} = W_d - W_w - W_H, \quad (2)$$

In which
$W_{AMPS,m}$—estimated AMPS monomer content after curing,
$W_d$—sample weight after drying,
$W_w$—dry sample weight after washing,
$W_H$—honey content as dry residual.

Concentration of AMPS monomer in hydrogel wa defined as percentage of $W_{AMPS,m}$ from total initial sample weight before drying (W)

Table 9 represents AMPS monomer content after curing, estimated using Flory-Rehner method for samples (2 to 8).

TABLE 9

Dry samples weight and monomer residuals according to Flory-Rehner method (2 to 8)

| Characteristic | Composition | | | | | | |
|---|---|---|---|---|---|---|---|
| | 2 | 3 | 4 | 5 | 6 | 7 | 8 |
| Dry sample weight after washing, $W_w$, gr | 16.2 | 15.8 | 28.8 | 25.6 | 31.1 | 27.3 | 27.5 |
| AMPS monomer estimated content after curing, $W_{AMPS, m}$, gr | 15.5 | 15.3 | 4.9 | 6.1 | 2.0 | 4.4 | 3.6 |
| Concentration of AMPS monomer (Flory-Rehner) in hydrogel, % w/w | 15.7 | 15.3 | 5.2 | 6.1 | 2.1 | 4.4 | 3.7 |

Note that concentration of AMPS monomer after curing estimated using Flory-Rehner method was higher than that estimated using TGA (see Table 4 for details), however general tendency is preserved. Thus, higher monomer concentration can be referred to weight loss during handling and other experimental errors.

Antibacterial Activity

In testing antibacterial activity, a wound dressing was prepared from a composition of 20% of honey, 0.05% of photo-initiator, 0.15% of linker, 1% HA, 53.15% AMPS, water added—to 100%.

The described method allows to manufacture active antibacterial bandages, which have been tested for Surgery Site Infection (SSI) prevention and treatment. SSI develops at about 10% of patients.

SSI prevention in patients of high risk group includes dressing of surgery site with sterile hyaluronic acid and honey-based hydrogel bandage just after the surgery, and reapplied within 24 hours up to 4 days (depending on wound condition).

Figure 6A:
FIGS. 6A-6B are photographic images of a post surgical knee dressing according to the present disclosure, to prevent surgery site infection (SSI), the dressing was applied immediately after surgery (FIG. 6A) and after four days when the patient was discharged with no risk of SSI development (FIG. 6B)
Figure 6B:

FIGS. 6A-6B represent an example of SSI prevention dressing, where the dressing was applied directly after the surgery (FIG. 6A) and reapplied once 12 hours after the surgery. Four days after the surgery the patient was discharged with no risk of SSI development (FIG. 6B). It is noted that in all the trials when hydrogel dressings have been applied, no SSI developed.

SSI treatment with the wound dressing disclosed herein included application of the dressing and periodical replacement until the surgery site was clean, and no inflammation was observed.

Figure 7A:
FIGS. 7A-7D are photographic images of an infected surgery site, three months post surgery (FIG. 7A), after 1 day of treatment with a wound dressing according to the present disclosure (FIG. 7B), 1 week of treatment (FIG. 7C) and after 1 month of complementary treatment with wound healing promoting system, used after the SSI treatment (FIG. 7D)
Figure 7B:
Figure 7C:
Figure 7D:

FIGS. 7A-7D represent the results of SSI treatment for a patient who suffered from SSI for 3 months after surgery. The surgery site condition before the treatment (3 months after the surgery) is shown in FIG. 7A; the surgery site condition 1 day after the treatment is shown in FIG. 7B; the surgery site condition at the end of treatment with hydrogel (circa 1 week of treatment) is shown in FIG. 7C. After the treatment stage (1 week), healing of the surgery site was accelerated using honey-based L-Mesitran Soft Gel. FIG. 7D represents surgery site condition 1 month after the healing stage started.

The results presented in FIGS. 6A-6B and 7A-7D clearly show that the wound dressing formed from 20% honey, 0.05% of photo-initiator, 0.15% of linker, 1% HA, 53.15%

AMPS was highly effective in preventing development of inflammation (FIG. 6B) as well as in healing SSI that has already developed.

Biocompatibility

The biocompatibility of the hydrogel was checked by NAMSA laboratories and showed good biocompatibility, as described below.

Cytotoxicity

Cytotoxicity test was conducted based on the requirement of ISO 10993-5 (BIOLOGICAL EVALUATION OF MEDICAL DEVICES-Part 5: Tests for in vitro cytotoxicity). Culture wells of a 6-well tissue culture plate that contained a sub-confluent monolayer of L-929 mouse fibroblast cells were used for testing. Triplicate wells were dosed with either the test article section (the wound dressing comprising the hydrogel and 20% honey, 0.05% initiator and 0.15 cross-linker), high density polyethylene as a negative control, or latex as a positive control. Each article (each of the test article or the controls) was placed in direct contact with the L-929 cells. After incubating for 24-26 hours, the cultures were examined microscopically (100×) for any abnormal cell morphology and cell lysis in proximity to the articles. The test article showed mild cytotoxicity to L-929 cells and was determined to meat the regulatory requirements.

Skin Sensitivity

The test article was further evaluated for the potential to elicit delayed dermal contact sensitization in the guinea pig. This study was conducted based on the requirements of ISO 10993-10 [BIOLOGICAL EVALUATION OF MEDICAL DEVICES, Part 10: Tests for irritation and skin sensitization].

The test article was patched, in an occlusive manner, to the intact skin of ten animals for 6 hours (+30 minutes), three times a week, over a 3-week period. The control article was similarly patched to five animals. Following a 2-week recovery period, the ten test and five control animals were patched, in an occlusive manner, with the test article and the control article. All sites were observed for evidence of dermal reactions at 24 and 48 hours after patch removal. The test article showed no evidence of causing delayed dermal contact sensitization in the guinea pig.

Skin Irritation

The product was evaluated for primary skin irritation in rabbits. This study was conducted in accordance with the guidelines of ISO 10993-10, Biological evaluation of medical devices-Part 10: Tests for irritation and skin sensitization. Two 25 mm×25 mm sections of the test article and control article were topically applied to the skin of each of three rabbits and left in place for a minimum of 23 hours and a maximum of 24 hours. The sites were graded for erythema and edema at 1, 24, 48 and 72 hours after removal of the single sample application. There was no erythema and no edema observed on the skin of the animals treated with the test article.

The Primary Irritation Index for the test article was calculated to be 0.0. The response of the test article was categorized as negligible

The invention claimed is:

1. A wound dressing composition comprising cross-linked hydrogel scaffold and embedded therein anti-bacterially active honey:
   wherein the wound dressing composition has an anti-bacterial activity that is determined by a detection of hydrogen peroxide production rate by the wound dressing composition;
   wherein the wound dressing composition further comprising at least one photo-initiator and at least one UV cross linker;
   wherein a total amount of the at least one photo-initiator and the at least one UV cross linker is equal or less than 0.2% w/w out of a total weight of the wound dressing composition;
   wherein an amount of the at least one UV cross linker does not exceed 0.15% w/w out of the total weight of the wound dressing composition; and
   wherein the amount of the at least one photo-initiator and the at least one UV cross linker is effective to provide the wound dressing composition with no detectable amount of free monomer units.

2. The wound dressing composition of claim 1, having a viscosity greater than 33,000 as determined by a viscometer using a T-Bar spindle at 12 rpm.

3. The wound dressing composition of claim 1, wherein the cross-linked hydrogel is comprised of sulfonate containing monomeric units.

4. The wound dressing composition of claim 3, wherein the sulfonate containing monomeric units comprises 2-Acrylamido-2-methylpropane sulfonic acid (AMPS).

5. The wound dressing composition of claim 1, wherein the cross-linked hydrogel comprises hyaluronic acid (HA).

6. The wound dressing composition of claim 1, comprising the anti-bacterially active honey in an amount of at least 5% w/w out of the total weight of the wound dressing composition.

7. The wound dressing composition of claim 1, wherein the hydrogen peroxide production rate is determined by a use of a hydrogen peroxide strip test according to manufacturer's instruction.

8. The wound dressing composition of claim 1, being embedded within or onto a support matrix.

9. The wound dressing composition of claim 1, having a saline or water holding capacity of at least 700 w % from the weight of the wound dressing composition.

10. A method of treating a wound or preventing a wound infection, the method comprising placing a wound dressing composition of claim 1, onto the wound.

11. A method of producing a wound dressing composition comprising cross-linked hydrogel scaffold and embedded therein anti-bacterially active honey, the method comprises:
   mixing a hydrogel forming mixture comprising hydrogel forming monomer or monomers, anti-bacterially active honey, at least one photo-initiator and at least one UV cross linker to form a homogenous mixture; and
   subjecting the homogenous mixture to UV irradiation until the homogenous mixture solidifies;
   wherein a total amount of the at least one photo-initiator and the at least one UV cross linker is equal or less than 0.2% w/w out of a total weight of the wound dressing composition;
   wherein an amount of the at least one UV cross linker does not exceed 0.15% w/w out of the total weight of the wound dressing composition; and
   wherein the amount of the at least one photo-initiator and the at least one UV cross linker is effective to allow complete cross-linking of monomers of the cross-linked hydrogel.

12. The method of claim 11, wherein said US the at least one UV cross linker comprises sulfonate-containing monomeric units.

13. The method of claim 11, wherein the sulfonate containing monomeric units comprises or is AMPS.

14. The method of claim 11, wherein the hydrogel forming mixture comprises hyaluronic acid (HA).

15. The method of claim 11, wherein the anti-bacterially active honey is in an amount of at least 5% w/w out of the total weight of the wound dressing composition.

16. The method of claim 11, comprising contacting the homogenous mixture with a supporting matrix prior to the UV irradiation.

* * * * *